US012806072B2

(12) United States Patent
Yin et al.

(10) Patent No.: US 12,806,072 B2
(45) Date of Patent: Nov. 24, 2026

(54) REGION-SPECIFIC IMAGE ENHANCEMENT FOR OPHTHALMIC SURGERIES

(71) Applicant: Alcon Inc., Fribourg (CH)

(72) Inventors: Lu Yin, Keller, TX (US); Vignesh Suresh, Woodland Hills, CA (US); Ramesh Sarangapani, Coppell, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/971,382

(22) Filed: Dec. 6, 2024

(65) Prior Publication Data

US 2025/0205081 A1 Jun. 26, 2025

Related U.S. Application Data

(60) Provisional application No. 63/614,706, filed on Dec. 26, 2023.

(51) Int. Cl.
*A61F 9/007* (2006.01)
*A61B 3/14* (2006.01)
(Continued)

(52) U.S. Cl.
CPC ................ *A61F 9/007* (2013.01); *G06T 5/60* (2024.01); *G06T 7/11* (2017.01); *G06T 7/90* (2017.01); *A61B 3/14* (2013.01); *A61B 2017/00203* (2013.01); *A61B 90/20* (2016.02); *A61B 2090/373* (2016.02); *A61B 2505/05* (2013.01); *G06T 2207/10024* (2013.01); *G06T 2207/20081* (2013.01); *G06T 2207/20084* (2013.01);
(Continued)

(58) Field of Classification Search
CPC ... G06T 7/11; G06T 7/90; G06T 2207/10024; G06T 2207/20104; G06T 2207/30041; A61B 3/0008; A61B 3/0025; A61B 3/14; A61B 3/13; A61F 9/007
See application file for complete search history.

(56) References Cited

U.S. PATENT DOCUMENTS 5,644,642 A * 7/1997 Kirschbaum .......... A61B 3/113 382/103
7,277,561 B2 * 10/2007 Shin ........................ G06V 40/18 382/117
(Continued)

FOREIGN PATENT DOCUMENTS

CA 2487411 C * 6/2011 ......... A61F 9/00806

*Primary Examiner* — Oommen Jacob
(74) *Attorney, Agent, or Firm* — Sanders IP Law

(57) ABSTRACT

A method for enhancing a digital image of a patient's eye includes illuminating the patient's eye with light from a modulable lighting source and collecting a digital image of the illuminated eye while the eye is tracked via motion tracking logic of an electronic control unit (ECU). The method includes receiving input signals as a request to enhance an area-of-focus of the eye, automatically identifying the area-of-focus via artificial intelligence (AI) logic in response to the input signals, and selectively adjusting characteristics of the lighting source and constituent pixels of the digital image located outside of the area-of-focus. The method further includes transmitting display control signals to one or more display screens to present an enhanced digital image of the eye. A system for enhancing the digital image includes the lighting source, digital camera, and ECU.

20 Claims, 6 Drawing Sheets

(51) Int. Cl.

| | |
|---|---|
| ***A61B 17/00*** | (2006.01) |
| ***A61B 90/00*** | (2016.01) |
| ***A61B 90/20*** | (2016.01) |
| ***G06T 5/60*** | (2024.01) |
| ***G06T 7/11*** | (2017.01) |
| ***G06T 7/90*** | (2017.01) |

(52) U.S. Cl.
CPC ............... *G06T 2207/20104* (2013.01); *G06T 2207/30041* (2013.01)

(56) References Cited

U.S. PATENT DOCUMENTS 7,798,643 B2* 9/2010 Waldorf ................. G08B 21/06 351/209
8,092,021 B1* 1/2012 Northcott ............. A61B 3/1015 351/221
8,345,936 B2* 1/2013 Burge .................... G06V 40/19 382/117
8,824,779 B1* 9/2014 Smyth ....................... G06T 7/73 382/117
8,861,799 B2* 10/2014 Savvides .............. G06V 40/172 382/117
9,053,524 B2* 6/2015 Florea ....................... G06T 7/11
9,421,131 B2* 8/2016 Watanabe .............. A61B 34/10
9,495,743 B2* 11/2016 Angeley ............... G06T 7/0012
9,704,038 B2* 7/2017 Wu ......................... G06F 3/013
11,341,222 B1* 5/2022 Caffey .................. H04W 12/06
12,047,717 B2* 7/2024 Myers .................... H04N 9/646
12,323,749 B2* 6/2025 Myers ................ G02B 21/0012
2006/0274213 A1* 12/2006 Saier .................. H04N 21/4318 348/673
2008/0044063 A1* 2/2008 Friedman ............. A61B 3/1216 382/117
2008/0253622 A1* 10/2008 Tosa ........................ G06T 7/149 382/117
2009/0247997 A1* 10/2009 Watanabe ........... A61F 9/00836 606/4
2009/0247998 A1* 10/2009 Watanabe ........... A61F 9/00827 606/5
2009/0279790 A1* 11/2009 Burge .................... G06V 40/19 382/209
2010/0014718 A1* 1/2010 Savvides ................ G06V 40/19 382/117
2010/0057059 A1* 3/2010 Makino .................. A61B 3/113 606/4
2011/0228975 A1* 9/2011 Hennessey ............. G06F 3/013 382/103
2012/0200689 A1* 8/2012 Friedman ............. G06V 40/166 348/78
2013/0088583 A1* 4/2013 Northcott ............... G06V 40/19 348/78
2013/0088584 A1* 4/2013 Malhas .................. G06V 40/19 348/78
2013/0329079 A1* 12/2013 Florea .................. G06V 40/162 348/222.1
2014/0161325 A1* 6/2014 Bergen ................... G06V 40/10 382/117
2014/0176906 A1* 6/2014 Chen ........................ A61B 3/14 351/206
2015/0320311 A1* 11/2015 Chen .................... G06V 10/993 351/246
2015/0324974 A1* 11/2015 Garber .................. G06T 7/0012 382/128
2016/0227113 A1* 8/2016 Horesh ................ H04N 23/611
2017/0251366 A1* 8/2017 Perna ...................... G06F 21/32
2017/0352135 A1* 12/2017 Florea ..................... G06T 7/181
2018/0173951 A1* 6/2018 Andorko ................... G06T 7/11
2018/0235456 A1 8/2018 Karakaya et al.
2019/0099226 A1* 4/2019 Hallen ..................... A61B 3/13
2019/0302460 A1* 10/2019 Kaul .................... G02B 27/017
2020/0160079 A1* 5/2020 Reda .................... G06V 10/454
2020/0257113 A1* 8/2020 Bednarik ............... A61B 3/113
2020/0327304 A1* 10/2020 Li .......................... G06V 40/19
2021/0019493 A1* 1/2021 Yokoyama ............. A61B 3/113
2021/0325649 A1* 10/2021 Segev .................. A61B 3/0008
2021/0383548 A1* 12/2021 Wilson ...................... G06T 5/70
2023/0152567 A1* 5/2023 Hewlett ............. G02B 21/0012 600/249
2025/0205081 A1* 6/2025 Yin ........................ A61B 3/132

* cited by examiner

REGION-SPECIFIC IMAGE ENHANCEMENT FOR OPHTHALMIC SURGERIES

CROSS-REFERENCE TO RELATED APPLICATIONS

The present application claims the benefit of priority to U.S. Provisional Application No. 63/614,706 filed Dec. 26, 2023, which is hereby incorporated by reference in its entirety for all purposes.

TECHNICAL FIELD

The present disclosure generally relates to automated digital image processing methodologies and related hardware solutions for selectively enhancing digital images of an eye during an ophthalmic surgery.

BACKGROUND

Modern surgical procedures may employ a surgical microscope to provide a surgeon with a magnified view of target anatomy. Target magnification allows the surgeon to perform delicate surgical procedures on miniscule anatomical features or tissues. During a microscope-assisted procedure or microsurgery, magnified stereoscopic digital images of the target anatomy may be displayed within an operating suite via one or more high-resolution display screens, a heads-up display, or a set of oculars. Presentation of the magnified images in such a manner allows the surgeon to accurately visualize the target anatomy when evaluating its health or when maneuvering a tool in the performance of a surgical task.

Real-time visualization of target anatomy during a microsurgery requires adequate task lighting. Surgical task lighting is often task-specific, with available lighting devices possibly including a microscope-mounted lamp, an overhead lighting array, a surgeon-worn headlight, and/or an endoilluminator. Each lighting device emits light in a particular wavelength range and color temperature. Surgical task illumination may coincide with digital image processing of collected image data to present a useful representation of the target anatomy to the surgeon within the operating suite.

SUMMARY

Disclosed herein are automated methods and hardware-based systems for selectively enhancing digital images in a region-specific manner, e.g., during performance of a visualization procedure or a microsurgery. In a representative ophthalmic context, for instance, the microsurgery may include cataract surgery, minimally invasive glaucoma surgery (MIGS), or vitreoretinal surgery, with these and other possible surgeries of the eye or other target anatomy of a human patient benefitting from the present teachings.

In accordance with the disclosure, real-time image segmentation and enhancement is performed by one or more processors of an electronic control unit (ECU), itself possibly constructed as one or more networked processors or computing nodes. The ECU separates a collected digital image into different surgeon-requested and/or ECU-requested regions after first using artificial intelligence (AI) logic to identify the requested region(s) in the digital image. The present strategy is readily customizable and possibly interactive, e.g., by considering specific clinical needs of the particular surgeon performing the procedure. Real-time digital images processed in the manner described below may help guide the surgeon during the procedure, for instance through presentation of an improved red reflex response as described below.

In particular, a representative computer-based method is disclosed herein for enhancing a digital image of a patient's eye during an ophthalmic surgery or other procedure. An implementation of the method may include illuminating the eye with light from a modulable lighting source, as well as collecting a digital image or images of the eye while the eye is illuminated with light from the modulable lighting source, and while the eye is tracked via motion tracking logic of the above-noted ECU. The method also includes receiving input signals via the ECU during the ophthalmic procedure, the input signals including a request to enhance an area-of-focus of the digital image, and identifying the area-of-focus via AI logic of the ECU in response to the input signals.

Additionally, the method in this particular embodiment includes selectively adjusting respective characteristics of the modulable lighting source and constituent pixels of the digital image located outside of the requested area-of-focus. This occurs via the ECU in response to the input signals. Display control signals are thereafter transmitted to one or more display screens to present an enhanced digital image of the patient's eye.

A system for enhancing a digital image of a patient's eye during an ophthalmic surgery is also disclosed herein. A non-limiting construction of the system includes a modulable lighting source, a digital camera, and an ECU. The modulable lighting source is operable for illuminating the patient's eye with light. The digital camera in turn is operable for collecting the digital image or images of the patient's eye as the eye is illuminated by the light and tracked by motion tracking logic. The ECU, which is in communication with the digital camera and the modulable lighting source, is configured to receive input signals. The input signals include a request to enhance an area-of-focus of the digital image.

Additionally, the ECU is operable for identifying the requested area-of-focus via AI logic in response to the input signals, with the AI logic including image segmentation logic, a neural network, and/or a trained model. As part of the ECU's envisioned construction, the ECU selectively adjusts respective characteristics of the modulable lighting source and the constituent pixels of the digital image located outside of the area-of-focus. This control action occurs in response to the input signals. As noted above, the ECU is also configured to transmit display control signals to one or more display screens to thereby present an enhanced digital image of the patient's eye.

A computer-readable storage medium is also disclosed herein on which is recorded instructions for enhancing a digital image of a patient's eye during an ophthalmic procedure. Execution of the instructions by one or more processors causes the processor(s) to receive a digital image or images of the eye from a digital camera, with the digital camera being in wired and/or wireless communication with the processor(s) as the eye is illuminated by light from a modulable lighting source and tracked via motion tracking logic. The processor in a possible implementation may be caused to receive input signals from a microphone. The input signals may be spoken utterances or phrases from a surgeon performing the ophthalmic procedure, such that the input signals include a request to enhance an area-of-focus of the digital image, e.g., a pupil, iris, sclera, or limbus region of the eye.

In this representative construction, execution of the instructions causes the processor(s) to identify the area-of-focus using AI logic, with this action occurring in response to the input signals. The processor then selectively adjusts respective characteristics of the modulable lighting source and constituent pixels of the digital image located outside of the area-of-focus in response to the input signals, and transmits display control signals to one or more display screens to thereby present an enhanced digital image of the patient's eye.

The above-described and other possible features and advantages of the present disclosure will be apparent from the following detailed description of the best modes for carrying out the disclosure when taken in connection with the accompanying drawings.

BRIEF DESCRIPTION OF THE DRAWINGS

The drawings described herein are for illustrative purposes only, are schematic in nature, and are intended to be exemplary rather than to limit the scope of the disclosure.

The above summary is not intended to represent every possible embodiment or every aspect of the subject disclosure. Rather, the foregoing summary is intended to exemplify some of the novel aspects and features disclosed herein. The above features and advantages, and other features and advantages of the subject disclosure, will be readily apparent from the following detailed description of representative embodiments and modes for carrying out the subject disclosure when taken in connection with the accompanying drawings and the appended claims.

DETAILED DESCRIPTION

Embodiments of the present disclosure are described herein. It is to be understood, however, that the disclosed embodiments are merely examples and other embodiments can take various and alternative forms. The Figures are not necessarily to scale. Some features could be exaggerated or minimized to show details of particular components. Therefore, specific structural and functional details disclosed herein are not to be interpreted as limiting, but merely as a representative basis for teaching one skilled in the art to variously employ the present disclosure.

Figure 1:
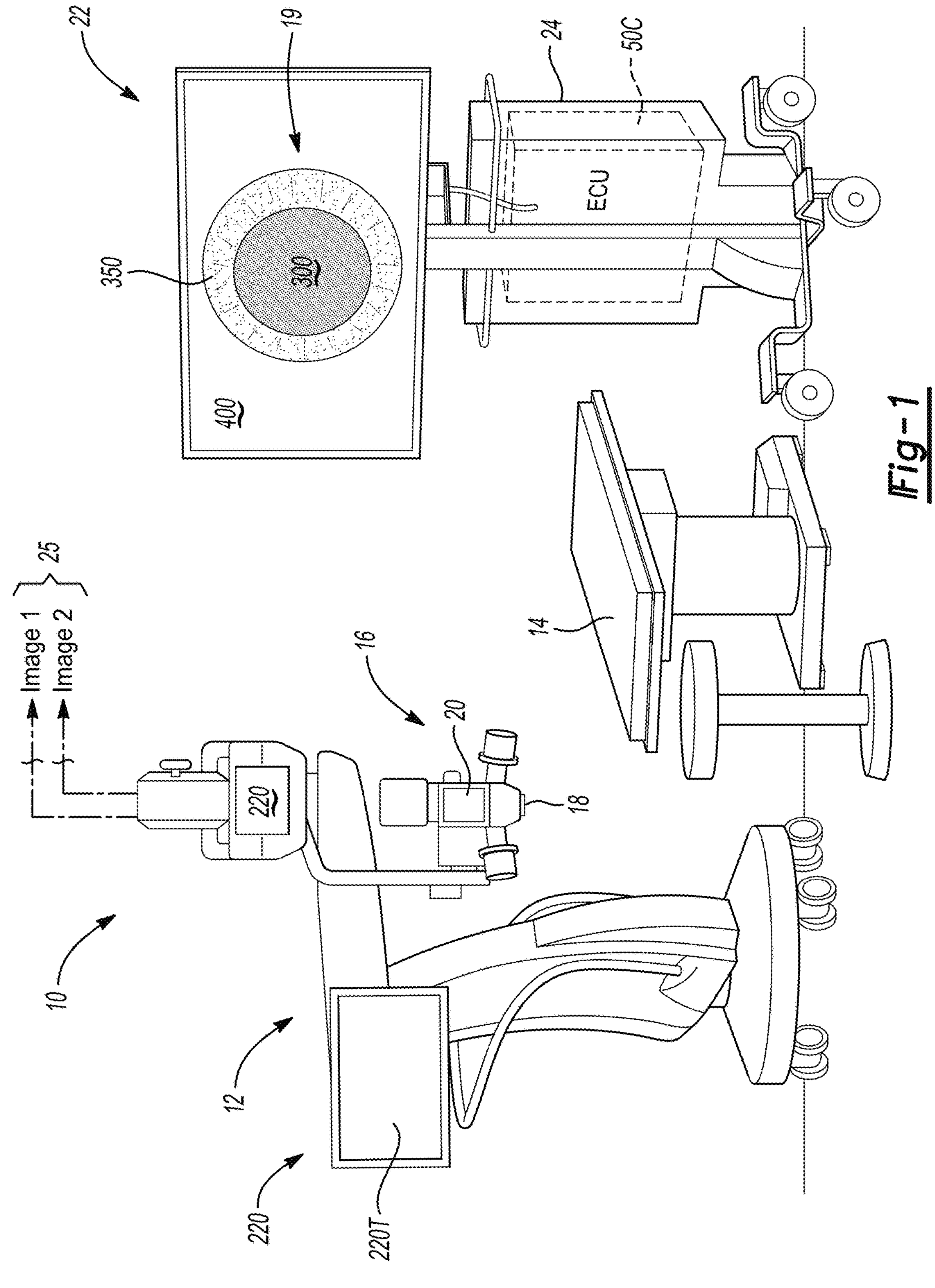
FIG. 1 illustrates a representative operating suite having an electronic control unit (ECU) configured to perform a digital image enhancement method in accordance with the present disclosure.

Referring now to the drawings wherein like reference numbers refer to like components, and beginning with FIG. 1, an operating suite 10 is depicted as it may appear during a representative eye surgery. As appreciated by those skilled in the art, the operating suite 10 may be equipped with a surgical robot 12 and an operating platform 14. The surgical robot 12 may be connected to a surgical microscope 16, e.g., a representative digital ophthalmic microscope, through which a surgeon (not shown) is able to view a patient's eye 30 (see FIG. 2) or other target anatomy under application-suitable levels of magnification. A modulable lighting source 18 and a digital camera 20 or one or more other image sensors may be coupled to or integral with the surgical microscope 16.

Using associated hardware and software of the surgical microscope 16 and an electronic control unit (ECU) 50C as described below, the surgeon is able to view magnified enhanced digital images 19 of the target anatomy. Visualization may be facilitated via one or more high-resolution display screens 22 and/or 220, one or more of which may include a touch screen 220T, e.g., a capacitive display surface. As shown, the enhanced digital images 19 are of the target eye 30 of FIG. 2, with the representative enhanced digital images 19 in FIG. 1 including a pupil 300, a surrounding iris 350, and portions of the sclera 400.

Figure 2:
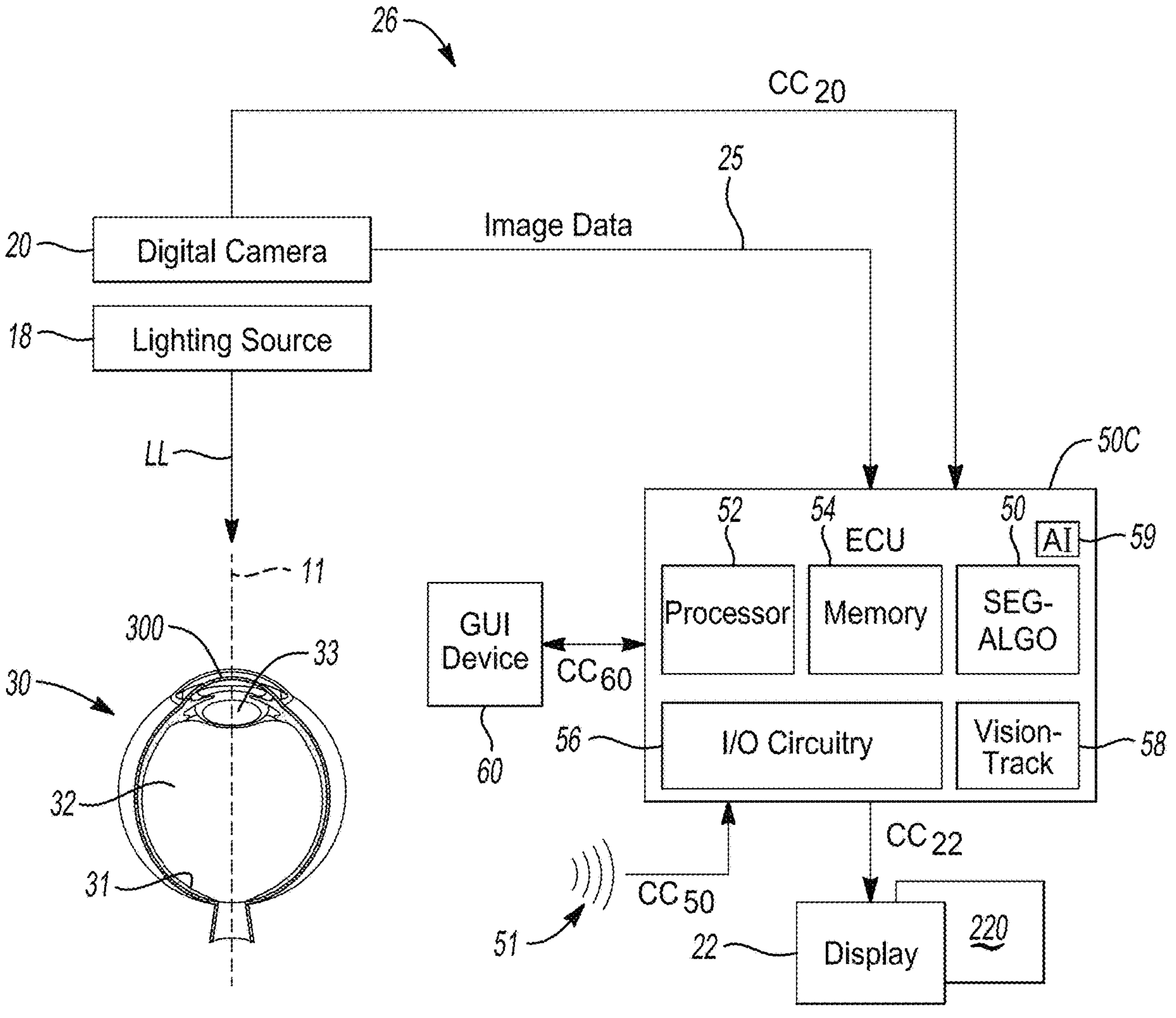
FIG. 2 is a schematic illustration of a system for performing digital image enhancement within the representative operating suite of FIG. 1.

Also present within the operating suite 10 is an optional cabinet 24 containing the ECU 50C, a processor 52 of which is shown in FIG. 2. The ECU 50C may be housed within the cabinet 24 in a possible implementation. Other embodiments are described below in which the processor 52 is integrated with or into other hardware within the operating suite 10 apart from the cabinet 24. Therefore, the illustrated implementation of FIG. 1 is non-limiting and exemplary, with the relevant processing functions of the ECU 50C and the processor(s) 52 described interchangeably below without regard to the particular location of either device.

The ECU 50C of FIG. 1 is configured herein to receive digital images (arrow 25), together forming a digital stereoscopic image as labeled "Image 1" and "Image 2" in FIG. 1. While collecting the digital images (arrow 25), the ECU 50C may execute computer-readable instructions embodying a method 50, an example of which is described below with reference to FIG. 5. The ECU 50C may be used as part of a system 26, representative hardware and software components of which are depicted in FIG. 2, with the system 26 in one or more implementations being operable for selectively enhancing the digital images (arrow 25) via surgeon input and/or autonomous functions of the ECU 50C in a region-specific manner as set forth below.

Real-time images of the patient's eye 30 during eye surgery tend to be rich in content, with the collected digital image (arrow 25) often showing a large part of the eye 30, possibly with different illumination patterns. However, at any given time during the course of an eye surgery, the surgeon may choose to focus on a relatively narrow region of the displayed digital image (arrow 25). The automated solutions disclosed herein are thus intended to reduce the surgeon's stress factor and improve surgical outcomes when using digital images (arrow 25), in particular by providing automated tools that functionally augment the digital image (arrow 25) within a desired area-of-focus.

In particular, the method 50 described herein provides localized image enhancement and image-guided surgical visualization for ophthalmic surgeries and other microsurgeries that combine the following concepts: (i) localization, (ii) image enhancement, and (iii) optional feedback. These three concepts are applied below in describing representative ophthalmic use cases, including cataract surgery, MIGS, and vitreoretinal surgery, without limiting the present teachings to such microsurgeries.

The ECU 50C depicted in FIG. 1 is programmed with instructions or computer-executable code embodying one or more algorithms when implementing the method 50. When performing the method 50, the ECU 50C may present enhanced digital images 19 via any or all of the display screens 22 and/or 220, which may be alternatively embodied as oculars, binoculars, or heads-up displays (HUDs). That is, the contemplated digital image processing functions are performed by the ECU 50C in real-time, and in an unobtrusive and transparent manner from the perspective of the surgeon, so that the enhanced digital images 19 ultimately have desired region-specific enhanced attributes.

Referring to FIG. 2, the patient's eye 30 is shown undergoing a microsurgery performed using the system 26 and its ECU 50C. During the microsurgery, the eye 30 may be illuminated by light (arrow LL) directed onto, and ultimately into, the eye 30 by the modulable lighting source 18, i.e., one having variable settings such as color, color temperature, brightness, etc. The modulable lighting source 18 may be embodied as one or more different lighting types such as lamps, light-emitting diode (LED) arrays, halogen devices, coaxial lighting sources, oblique lighting sources, and/or other suitably configured modulable lighting source 18 coupled to or integrally constructed with the surgical microscope 16 shown in FIG. 1.

In a possible embodiment, the light (arrow LL) may be a form of white light, e.g., warm white light having a color temperature of less than about 4500° K. The color, color temperature, brightness, and/or other possible characteristics of the light (arrow LL) may be selectable by the surgeon in response to input signals ($CC_{50}$) to the ECU 50C, e.g., as stated or uttered voice commands 51. For example, the modulable lighting source 18 may be configured as a red, green, blue (RGB) diode array or other lighting system having a variable output, including red, green, and blue light, individually or collectively. The modulable lighting source 18 may output the light (arrow LL) outside of the visible spectrum in some implementations, e.g., as near infrared, ultraviolet, etc.

The system 26 of FIG. 2 in the illustrated exemplary embodiment also includes the above noted digital camera 20. The digital camera 20 is operable for collecting digital images (arrow 25) as pixel image data of the patient's eye 30 under surgeon-selectable and/or procedure-specific illumination conditions. In an exemplary embodiment, the digital camera 20 may include a high-dynamic range (HDR) digital camera of the above-noted surgical microscope 16 of FIG. 1. Thus, components of the system 26 may be integral with the surgical microscope 16, i.e., an assembled internal or attached external component thereof, with the process steps of the method 50 of FIG. 6 being programmed functionality of the surgical microscope 16.

Other embodiments may be realized in which instructions embodying the method 50 are recorded on a non-transitory computer-readable storage medium, e.g., in memory 54 of the ECU 50C, and executed by the processor(s) 52 of the ECU 50C as shown, or one or more processors 52 located apart from the ECU 50C in other embodiments. Such structure would allow the ECU 50C to cause disclosed actions of the system 26 to occur. As noted above, the processor(s) 52 in alternative embodiments may be integrated into other hardware, e.g., the surgical microscope 16 and/or the digital camera 20, with inclusion of the processor(s) 52 in the construction of the ECU 50C being non-limiting.

During predetermined stages of the representative eye surgery during which the surgeon desires to test and evaluate the red reflex of the patient's eye 30, with such stages of the ophthalmic procedure possibly identified by the ECU 50C as an identified stage, the ECU 50C causes the modulable lighting source 18 to emit the light (arrow LL). This action may entail simply turning on the modulable lighting source 18 at the onset of the microsurgery. At the same time, the ECU 50C may command the digital camera 20, e.g., via corresponding camera control signals (arrow $CC_{20}$), to collect the digital images (arrow 25). The collected digital images (arrow 25) may be communicated or transmitted over transfer conductors and/or wirelessly to the processor (s) 52 for execution of the various digital image processing steps embodying the method 50.

When selectively enhancing the digital images (arrow 25), the processor(s) 52 of FIG. 2 may output a video display control signals (arrow $CC_{22}$) to the display screen(s) 22 and/or 220 to thereby cause the display screen(s) 22 and/or 220 ("Display(s)") to display a magnified dynamic image of the patient's eye 30. At other times, the digital camera 20 may be used as needed to image the eye 30, with possible illumination using light from other parts of the electromagnetic spectrum as needed in the surgeon's discretion.

The ECU 50C is depicted schematically in FIG. 2 as a unitary box solely for illustrative clarity and simplicity. Implemented embodiments of the ECU 50C may include one or more networked computer devices each with the processor(s) 52 and sufficient amounts of memory 54, the latter including a non-transitory (e.g., tangible) computer-readable storage medium on which is recorded or stored a set of computer-readable instructions, with such instructions embodying the segmentation and enhancement ("Seg-ALGO") functions of the method 50 being readable and executable by the processor(s) 52. An optional graphical user interface (GUI) device 60 may be used to facilitate intuitive interactions of the surgeon and attending surgical team with the system 26 via electronic output signals ($CC_{60}$) to the ECU 50C, with the electronic output signals ($CC_{60}$) being representative of the surgeon's inputs to the GUI device 60.

The memory 54 may take many forms, including but not limited to non-volatile media and volatile media. Instructions embodying the method 50 may be stored in the memory 54 and selectively executed by the processor(s) 52 to perform the various functions described below. The ECU 50C, either as a standalone device or integrated into the digital camera 20 and/or the surgical microscope 16 of FIG. 1, may also include resident machine vision/motion tracking logic 58 ("Vision-Track") for tracking movement of the eye 30 during the microsurgery, and possibly performing other tasks like identifying a surgical tool and/or the surgeon, which may occur during the course of eye surgery as set forth below.

As will be appreciated by those skilled in the art, non-volatile computer readable storage media may include optical and/or magnetic disks or other persistent memory, while volatile media may include dynamic random-access memory (DRAM), static RAM (SRAM), etc., any or all which may constitute part of the memory 54 of the ECU 50C. The input/output (I/O) circuitry 56 may be used to facilitate connection to and communication with various peripheral devices used during the surgery, inclusive of the digital camera 20, the modulable lighting source 18, and the high-resolution display screen(s) 22 and/or 220. Other hardware not depicted but commonly used in the art may be included as part of the ECU 50C, including but not limited to a local oscillator or high-speed clock, signal buffers, filters, amplifiers, etc.

Still referring to FIG. 2, performance of the method 50 by the ECU 50C as noted above enables localized image enhancement and image-guided surgical visualization for ophthalmic surgeries and other microsurgeries that combine three concepts: (i) localization, (ii) image enhancement, and (iii) optional feedback. Localization as contemplated herein may entail the use of artificial intelligence (AI) logic 59 of the ECU 50C to identify an area-of-interest in the digital image(s) (arrow 25) in real-time, and to highlight the identified area-of-focus via control of the modulable lighting source 18 and possible digital manipulation of constituent pixels of the digital image (arrow 25) during a given procedure. This in turn allows the processor(s) 52 to comprehend the digital image (arrow 25) and selectively enhance regions thereof.

Image enhancement involves the application of various image optimization and enhancement strategies within the identified area-of-focus, e.g., using quantifiable visual image quality metrics. Feedback may be used, e.g., in a closed-loop using zoom features of the surgical microscope 16 and/or illumination control of the modulable lighting source 18, to realize the localization and image enhancement functionality. For instance, targeted surgeon voice commands 51 such as "enhance red reflex", "focus on iris", "auto-center and auto-zoom on pupil", or "auto-white on sclera" may trigger corresponding actuation states of a microscope motor and particular digital processing actions when rendering a view of the digital image (arrow 5).

The ECU 50C may also be configured in or more embodiments to selectively enhance segmented regions of the patient's eye 30 in the digital image data (arrow 25), e.g., to optimize the red reflex response. As appreciated in the art, a surgeon may wish to detect and evaluate reflective performance of the patient's eye 30 in response to incident light during cataract surgery. The term "red reflex" refers to a detectable reflective phenomenon that normally occurs when light enters the pupil 300 and reflects off of the retina 31 at the posterior of the vitreous cavity 32. Red reflex tests are frequently used by eye surgeons and other clinicians to detect possible abnormalities of the eye's posterior anatomy.

Also detectable via red reflex tests are opacities located along the optical axis 11, likewise shown in FIG. 2 along with the pupil 300 and a lens 33. Such opacities are often present due to cataracts, for example, with cataracts leading to a progressive clouding of the lens 33. Other possible causes of a poor red reflex include corneal scarring and vitreous hemorrhage. The absence of a proper red reflex response is therefore of interest to a surgeon when diagnosing or treating various ocular conditions.

The present automated strategy may be illustrated by way of four representative use cases: (i) enhancing the red reflex within the imaged pupil 300 through digital and/or physical means while maintaining a 'normal' view of the sclera 400 (see FIG. 1), such as during a cataract surgery, (ii) blending of different illumination types, e.g., coaxial and oblique light of the modulable lighting source 18, and then choosing an optimal illumination color temperature to improve the red reflex and the general surgical view, e.g., for a patient having different cataract grades and/or eye pigmentation, (iii) enhancing visualization of a trabecular meshwork or other pertinent ocular features of the patient's eye 30 by adjusting spectral characteristics of the illumination, according to the pigmentation of the iris, e.g., for a wide range of MIGS devices, and (iv) improving visualization by adjusting image gamma of the digital image (arrow 25) to reduce intensity of specular reflectance in the area-of-focus, i.e., the relationship between stored pixel values and real-world luminance, to improve image clarity under glare and minimize visual comfort by reducing the intensity of specular reflectance. Each of these representative use cases will now be described in further detail with reference to FIGS. 3A-6.

Figure 3A:
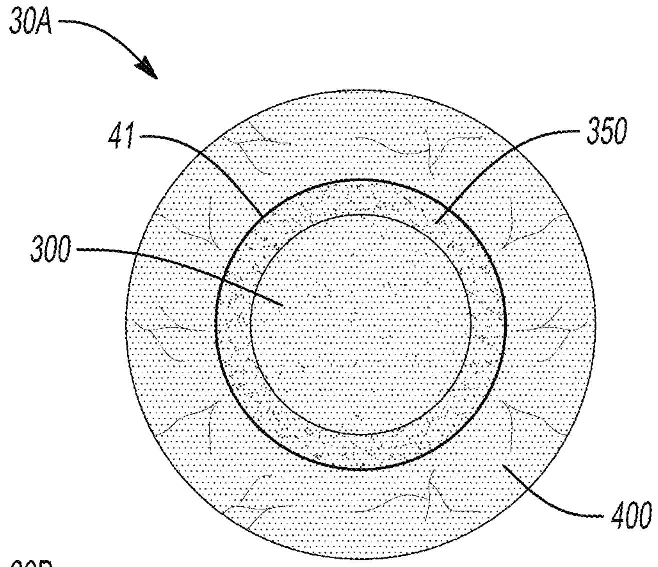
FIGS. 3A, 3B, and 3C illustrate different illuminated views of a patient's eye during a representative eye surgery.
Figure 3B:
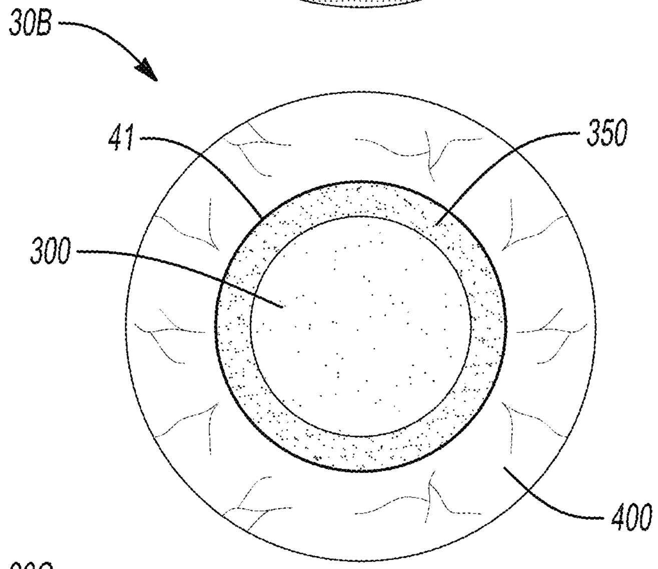
Figure 3C:
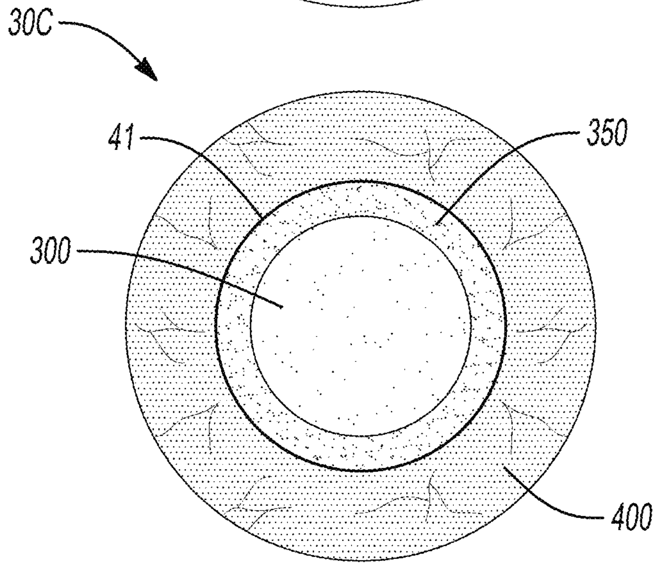
Figure 4A:
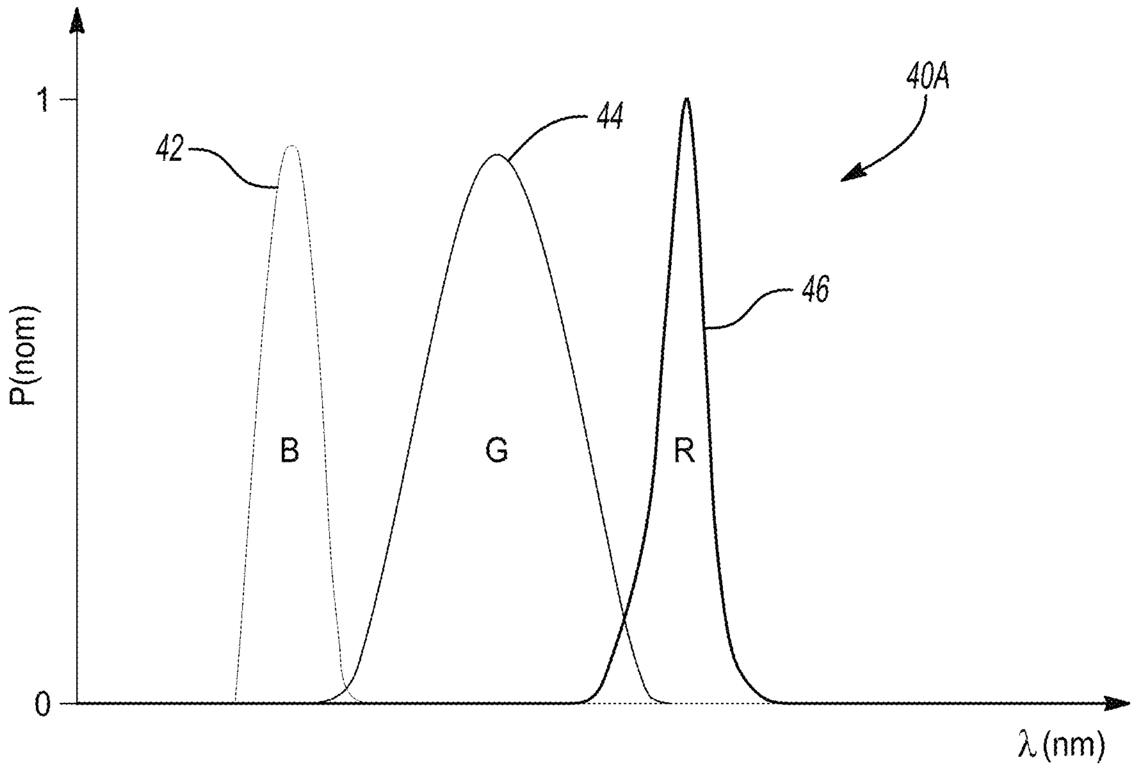
FIG. 4A is a plot of normalized power (vertical axis) versus wavelength (horizontal axis) corresponding to FIG. 3A.
Figure 4B:
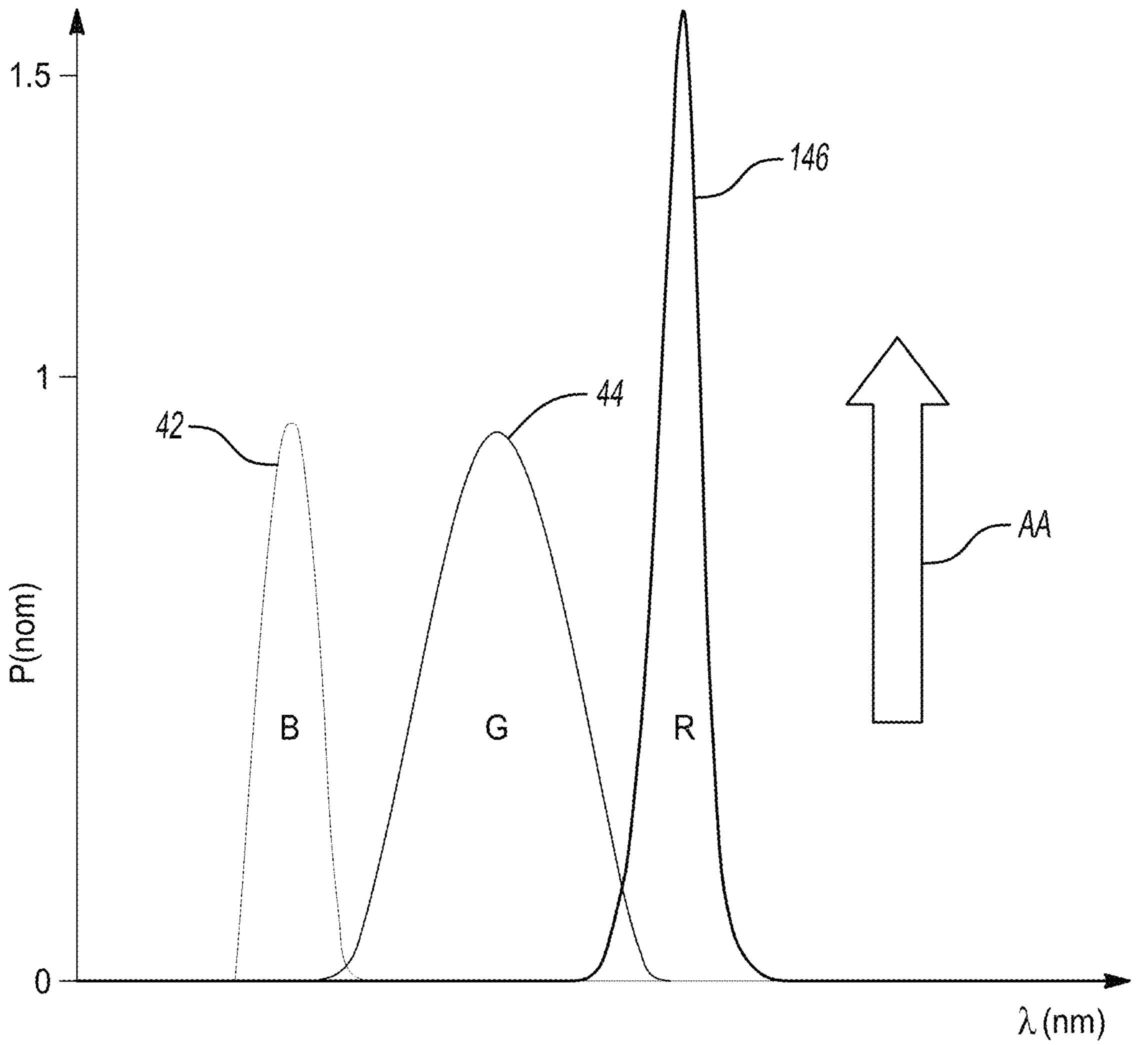
FIG. 4B is a plot of normalized power (vertical axis) versus wavelength (horizontal axis) corresponding to FIGS. 3B and 3C.

Referring to FIGS. 3A-3C in conjunction with plots 40A and 40B of FIGS. 4A and 4B, FIG. 3A represents a typical illuminated digital view of the patient's eye 30 of FIG. 2 during a representative cataract surgery. The illuminated eye 30A of FIG. 3A, with a circular perimeter 41 of the iris 350, is illustrated with 'normal' or full spectrum white light illumination. Such illumination may be provided by relatively balanced blue (B), green (G), and red (R) light components 42, 44, and 46 as shown in the nominal/normalized power plot 40A of FIG. 4A, with nominal power ($P_{nom}$) illustrated on the vertical axis and wavelength ($\lambda$) in nanometers (nm) depicted on the horizontal axis.

FIG. 3B illustrates the patient's eye 30 of FIG. 2 as an illuminated eye 30B, in particular one that is illuminated with an increased red light component 146. That is, the surgeon may wish to boost the red light component 46 of FIG. 4A as indicated by upward arrow AA of FIG. 4B, such as via a voice command such as "increase red light" or "boost red", thus forming the red light component 146. The ECU 50C may be calibrated to boost a particular requested light component 42, 44, or 46 by a set amount, e.g., 25-50%, with the surgeon possibly uttering the above phrases multiple times to boost to a desired level, or the surgeon may simply utter a more descriptive phrase such as "boost red 10", "boost red 25", etc., to command a corresponding percentage increase in the nominal power ($P_{nom}$) for that particular color.

Note that in FIG. 3B, the color appearance of the eye structure, including the sclera 400 located radially outside of the circular perimeter 41, also changes when this occurs. That is, the increased level of the exemplary red light component 146 falls incident upon all exposed surfaces area of the illuminated eye 30B. So, while the red light component 146 may enhance the red reflex in this particular example, the overall appearance of the illuminated eye 30B may not be desirable to the particular surgeon performing the procedure. The present method 50 thus allows the surgeon to freely customize the appearance of the display images.

FIG. 3C illustrates an example of this customization as an illuminated eye 30C. In this instance, visualization benefits are provided by the ECU 50C in segmenting and tracking only the limbus region, i.e., the approximately 1-2 mm wide transitional band of the patient's eye 30 located between the sclera 400 and the cornea covering the iris 350 and pupil 300. The illumination of plot 40B may still be applied. However, in this instance a color transformation may be applied by the ECU 50C outside of the limbus region, with the ECU 50C displaying the limbus region with an enhanced red reflex while presenting the remainder of the displayed image of the illuminated eye 30C with normal/full spectrum white light illumination. The programmed capability of the ECU 50C to do this will now be described using several use cases for various ophthalmic procedures, without limiting the present teaching to the described examples.

Use Case #1: as noted above, red reflex is the light reflected back from the eye 30 of FIG. 2 during cataract surgery, which creates contrast between materials of the lens 33 and surrounding anatomy. The method 50 may be used to selectively enhance the red reflex specifically within the limbus or pupil 300, while at the same time maintaining relatively constant visualization of structure of the eye 30 located outside of the pupil 300.

The ECU 50C as contemplated herein may proceed as follows: (i) using the AI logic 59, the segmentation algorithm 50 (method 50), and the vision tracking algorithm 58 (FIG. 2), the ECU 50C ultimately locates, identifies, and segments the pupil 300, limbus, or other surgeon-specified region of the patient's eye 30 in real-time, (ii) the ECU 50C commands a light source, e.g., the modulable lighting source 18 of FIGS. 1 and 2, to increase light energy in a specific color range, in this example red light, and quantify the illumination change(s) using colorimetric terms, e.g., International Commission on Illumination (CIE) XYZ, or color temperature, and (ii) the ECU 50C may use programmed color transformation logic recorded in memory 54 to shift the color appearance of eye structure located outside of the pupil 300 or limbus under the increased red light conditions of FIG. 4B, thereby enabling the surgeon to view the patient's eye 30 as if the eye 30 would appear when illuminated by warm, cool, or neural white light. For applications lacking modulable illumination, the ECU 50C may instead use digital red reflex enhancements to the desired region of the eye 30, in this case within the pupil 300 for red reflex enhancement. Digital enhancement may be used in combination of segmentation of the pupil 300, e.g., as described in U.S. patent application Ser. No. 17/507,082 to Yin et al., now published as US Patent Application Publication No. 2022/0198653A1, which was published on Jun. 23, 2022 and is hereby incorporated by reference in its entirety.

Use Case #2: the surgical microscope 16 of FIG. 1, e.g., for cataract surgery, such as the commercially available Alcon LuxOR® Revalia™ Ophthalmic Microscope, may be used to provide a blend of light for illumination of the patient's eye 30, such as coaxial and oblique light from respective coaxial and oblique lighting sources of the modulable lighting source 18. As appreciated in the art, coaxial light is useful for creating the above-described red reflex, while oblique light helps illuminate eye features such as the limbus/sclera 400. The optimal combination of coaxial and oblique light for visualization depends on the severity of the patient's cataract, pigmentation of the eye 30, etc. For some surgical microscopes 16, there may be multiple choices of color temperature for the illumination, such as but not limited to warm white, cool white light, and mixed white light. Selectively adjusting the respective characteristics of the modulable lighting source 18 and constituent pixels of the digital image (arrow 25) located within the area-of-focus may therefore include blending lighting from the coaxial and oblique lighting sources to optimize a red reflex of the patient's eye 30.

The method 50 proposed herein in non-limiting Use Case #2 may include performing the following process steps via the ECU 50C: (i) segmenting the digital image (arrow 25) of the patient's eye 30 of FIG. 2 into different anatomical regions, for instance the pupil 300 within the limbus or the sclera 400 located outside of the limbus, (ii) calculating visual metrics for relevant characteristics such as contrast and sharpness of the segmented ocular regions, and (iii) using such visual metrics to define an illumination configuration having an application-suitable blending of absolute power and, e.g., coaxial and oblique light. In addition, color distribution of pixels in the segmented region of the sclera 400 in this instance can be used to choose the color temperature of the illumination as well as white balancing of the digital image 25.

Use Case #3: in minimal invasive glaucoma surgery (MIGS), certain MIGS devices are inserted into the patient's eye 30 in close proximity to the trabecular meshwork, which in turn is located between the cornea 301 and the iris 350 (see FIGS. 3A-3C). For patients having varying degrees of eye pigmentation, or for eyes 30 of multiple patients having different pigmentation, i.e., blue, green, brown, hazel, etc., different illumination characteristics may be used to improve the contrast of the trabecular meshwork. Thus, aspects of the method 50 may entail detecting a pigmentation color of the patient's eye 30, and then adjusting spectral characteristics of the modulable lighting source 18 based on the detected pigmentation color.

The method 50 proposed herein may be implemented by the ECU 50C according to the following steps: (i) segmenting the view through the surgical microscope 16 into different anatomical regions, in particular within the iris 350 and its boundaries in this example, (ii) estimating the color of iris 350 and its adjacent region, e.g., using machine vision capabilities or inputs from the surgeon, and (iii) adjusting the color of the illumination by the modulable lighting device 18 of FIGS. 1 and 2 according to the color of the iris 350.

Use Case #4: during vitreoretinal surgery, the posterior chamber of the patient' eye 30 is illuminated by directed light, such as a light pipe/endoilluminator. Illumination in this manner creates a large intensity variation between regions within the displayed view. For some procedures such as an air-fluid exchange, which temporarily replaces the aqueous humor of the eye 30 with air to maintain its shape, strong specular reflection and diffusive glare are common.

Figure 5:
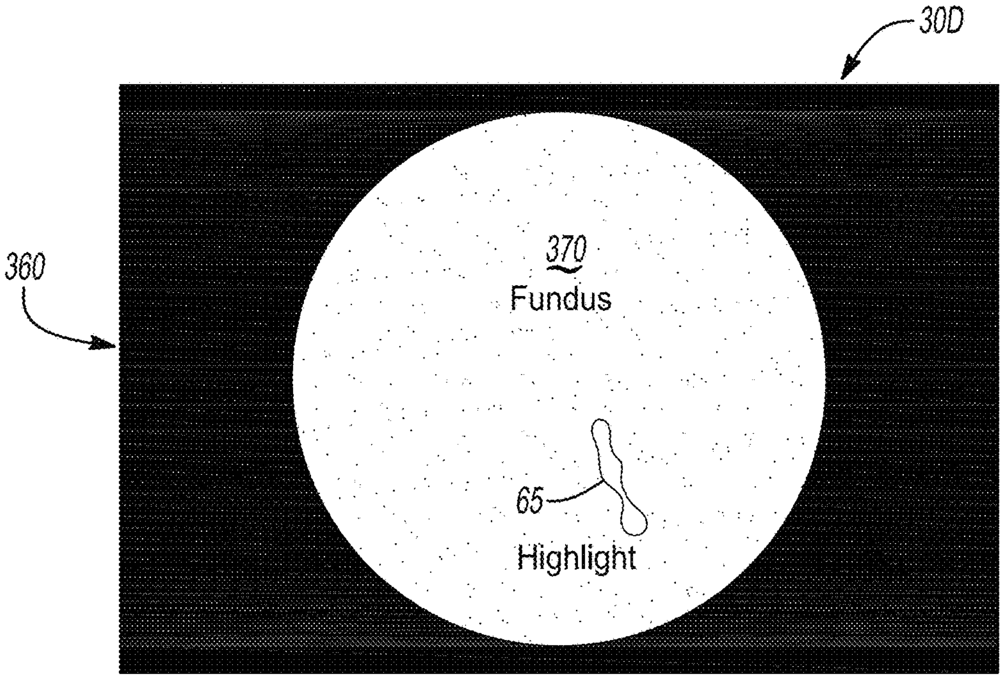
FIG. 5 is an illustration of a representative view of an image of a patient's eye during a vitreoretinal surgery.

A representative glare region is illustrated in FIG. 5 as a highlight 65 within a displayed image of a fundus region 370 of an illuminated eye 30D, with the fundus region 370 surrounded by a dark region 360 in the image. For improved visualization, image intensity adjustment (tone mapping) may be applied onto the digital image (arrow 25 of FIGS. 1 and 2) by the ECU 50C, with the ECU 50C considering image intensity distribution within each of the segmented regions. As noted above, the method 50 may include adjusting image gamma of the digital image (arrow 25) to reduce intensity of specular reflectance in the area-of-focus, e.g., due to the highlight 65 or another high-glare region.

The method 50 when performed during representative Use Case #4 may proceed via the following process steps: (i) detecting different intensity regions such as the dark region 360, the highlight 65, and the fundus region 370, and thereafter estimating statistics of a pixel intensity distribution within each of the constituent regions, (ii) using the calculated intensity statistics to define a tone mapping function for the digital image (arrow 25 of FIGS. 1 and 2), which would improve image clarity of regions impacted by the diffusive glare of the representative highlight 65 and minimize its intensity, and which would avoid amplifying the noise signal in the dark region 360, and (iii) adjusting intensity in concert with controlling overall illumination power of the modulable lighting source 18.

Figure 6:
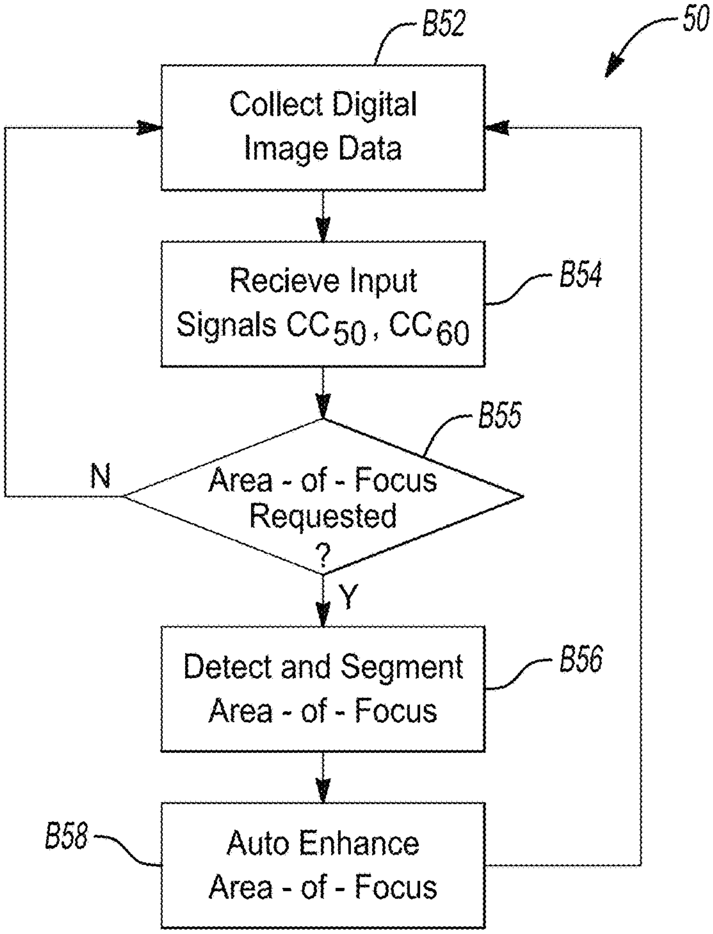
FIG. 6 is a flow chart describing a method for performing region-specific image engagement in accordance with the present disclosure.

Referring now to FIG. 6, a non-limiting embodiment of the method 50 for enhancing digital images during a microsurgery, e.g., of the patient's eye 30 during an eye surgery or another ophthalmic procedure, may be performed by the ECU 50C of FIGS. 1 and 2. The method 50 is described in terms of discrete process steps, algorithm code segments, or "blocks" for clarity, with each block of the method 50 being executed by the processor(s) 52 of the ECU 50C in the course of a microsurgery.

Beginning with block B52, the method 50 includes illuminating the patient's eye 30 with light from a modulable lighting source, e.g., the light (arrow LL) and modulable lighting source 18 of FIG. 2. As noted above, the modulable lighting source 18 may be connected to or integral with an ophthalmic microscope when the surgical microscope 16 is constructed in this manner. In some instances, illuminating the patient's eye 30 with light (arrow LL) from the modulable lighting source 18 may include illuminating the patient's eye 30 with white light.

The method 50 also includes collecting digital image data of the patient's eye 30. Block B52 may entail collecting a digital image or multiple images (arrow 25 of FIGS. 1 and 2) of the patient's eye 30 using the digital camera 20 as the eye 30 is illuminated in this manner, and while the eye 30 is tracked via the vision tracking algorithm 58 or other suitable motion tracking logic of the ECU 50C.

As appreciated in the art, full spectrum white light uses the full wavelength range of human-visible light, conventionally defined as about 380 nanometers (nm) to about 700 nm. In addition to wavelength, visible light/white light is often described in terms of its color temperature using descriptions such as "warm white", "daylight white", and "cool white". Color temperature is generally expressed in degrees Kelvin (° K), with warm white light in particular typically referring to light having a color temperature of less than about 4000° K. Such light falls predominantly within the orange and red ranges of full spectrum light. In contrast to warm white light, cool white light has a higher color temperature of about 5500° K to 7000° K or more, and is often dominated by blue light. Daylight white light falls somewhere between the conventionally defined color temperature limits of warm white light and cool white light. Any or all such varieties of white light may be used to illuminate the eye 30 in one or more of the embodiments contemplated herein.

At block B52, the method 50 includes receiving the input signals ($CC_{50}$ and/or $CC_{60}$) via the ECU 50C of FIGS. 1 and 2. In some implementations, block B52 may include receiving a request to enhance an area-of focus of the digital image (arrow 25). For example, the ECU 50C may receive voice commands 51 (FIG. 2) from the surgeon while the surgeon performs eye surgery or another ophthalmic procedure, with the voice commands 51 including an utterance or statement of a desired region of the patient's eye 30. For instance, a surgeon viewing the image of FIG. 3A may utter the phrase "detect limbus region" or "detect pupil". The voice commands, or possibly touch inputs to the GUI device 60, are then translated by the processor(s) 52 into computer-readable instructions and temporarily saved to memory 54. In embodiments in which the ECU 50C identifies a stage of the ophthalmic procedure as an identified stage, the ECU 50C may autonomously generate the input signals ($CC_{50}$ and/or $CC_{60}$) during the ophthalmic procedure based on the identified stage. The method 50 then proceeds to block B55.

Block B55 entails determining, via the ECU 50C, whether the input signals ($CC_{50}$ and/or $CC_{60}$) from block B54 correspond to a request for a particular area-of-focus, or a change to a previously requested area-of-focus. The method 50 proceeds to block B56 when the surgeon has requested or changed the area-of-focus, and repeats block B52 in the alternative when the surgeon has not requested or changed the area-of-focus.

At block B56, the ECU 50C identifies and segments corresponding pixels of the area-of-focus in response to the input signals ($CC_{50}$ and/or $CC_{60}$) of block B54 and B55, e.g., using artificial intelligence (AI) logic 59 of the ECU 50C and vision-tracking algorithm 58 of FIG. 2. In response to the input signals ($CC_{50}$ and/or $CC_{60}$), the surgeon-commanded or procedure-specific area-of-focus is detected in the digital image (arrow 25) by the ECU 50C.

As appreciated by those skilled in the art, the control actions performed by the ECU 50C in block B56 may include using edge detection techniques to identify telltale discontinuities in pixel intensity corresponding to edges of areas of interest in the image, or the use of feature matching via neural networks or other prior-trained models of the patient's eye 30. When the regions of interest have distinctive shapes or contours, the ECU 50C may use an optional Hough transform or other application-suitable technique to detect such features. Likewise, the pixel color, brightness, or other characteristics may be segmented into different regions to enable identification of the area-of-focus desired by the surgeon. The method 50 then continues to block B58.

Block B58 includes selectively adjusting respective characteristics of the modulable lighting source 18 and/or constituent pixels of the digital image (arrow 25( ) located outside of the area-of-focus. This action occurs via the ECU 50C in response to the input signals ($CC_{50}$ and/or $CC_{60}$). Block B58 may include enhancing the constituent pixels of the area-of-focus from block B56 to differentiate the area-of-focus from the surrounding area and enhance the resulting image presentation. Block B58 may also include transmitting display control signals (arrow $CC_{22}$ of FIG. 2) to one or more of the display screens 22 and/or 220 to thereby present the enhanced digital image 19 of the patient's eye 30.

In the exemplary red reflex scenario of FIG. 3C, the ECU 50C may, as part of block B58, selectively increase the red light component 44 of the modulable lighting source 18 as shown in FIG. 4B, but without doing so for the entire imaged scene. That is, the ECU 50C may isolate the limbus region from the sclera 400, digitally manipulating pixel characteristics of pixels corresponding to the sclera 400 so that such pixels appear as they would under normal white lighting conditions, or under other specifically-requested lighting conditions. The method 50 may also include digitally decreasing a brightness and/or color temperature of the constituent pixels of the digital image (arrow 25) located outside of the area-of-focus, thus leaving the area-of-focus with an enhanced appearance. The method 50 then returns to block B52 and continues in a loop during the ophthalmic surgery.

As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

The detailed description and the drawings are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A method for enhancing a digital image of a patient's eye during an ophthalmic procedure, comprising:

illuminating the patient's eye with light from a modulable lighting source;

collecting the digital image of the patient's eye while the patient's eye is being illuminated with the light from the modulable lighting source;

receiving input signals during the ophthalmic procedure, the input signals including a request to enhance an area-of-focus of the digital image;

in response to the input signals, selectively adjusting respective characteristics of the modulable lighting source and digitally adjusting characteristics of only those constituent pixels of the digital image that are located outside of the area-of-focus; and transmitting display control signals to one or more display screens to thereby present an enhanced digital image of the patient's eye.

2. The method of claim 1, wherein the modulable lighting source is connected to or integral with an ophthalmic microscope, and wherein illuminating the patient's eye with the light from the modulable lighting source includes illuminating the patient's eye with white light.

3. The method of claim 1, wherein receiving input signals includes receiving voice commands from a surgeon while the surgeon performs the ophthalmic procedure.

4. The method of claim 3, wherein the voice commands include an utterance or statement of a desired region of the patient's eye, the desired region including a pupil, an iris, a sclera, or a limbus region.

5. The method of claim 1, further comprising:

identifying a stage of the ophthalmic procedure as an identified stage; and autonomously generating the input signals during the ophthalmic procedure based on the identified stage.

6. The method of claim 1, wherein collecting the digital image of the patient's eye is performed using a high-dynamic range (HDR) digital camera.

7. The method of claim 1, further comprising identifying the area-of-focus via artificial intelligence (AI) logic in response to the input signals.

8. The method of claim 7, wherein identifying the area-of-focus via the AI logic includes processing the digital image via a neural network and/or a trained model.

9. The method of claim 1, wherein selectively adjusting the respective characteristics of the modulable lighting source and digitally adjusting characteristics of only those constituent pixels of the digital image that are located outside the area-of-focus includes:

increasing a red light component of the modulable lighting source; and/or digitally decreasing a brightness and/or color temperature of the constituent pixels of the digital image located outside of the area-of-focus.

10. The method of claim 1, wherein the modulable lighting source includes a coaxial lighting source and an oblique lighting source, and wherein selectively adjusting the respective characteristics of the modulable lighting source includes blending lighting from the coaxial lighting source and the oblique lighting source to optimize a red reflex of the patient's eye.

11. The method of claim 1, further comprising:

detecting a pigmentation color of an iris of the patient's eye, wherein selectively adjusting the respective characteristics of the modulable lighting source includes adjusting spectral characteristics of the modulable lighting source based on the pigmentation color.

12. The method of claim 1, wherein selectively adjusting the respective characteristics of the modulable lighting source and digitally adjusting characteristics of only those constituent pixels of the digital image that are located outside the area-of-focus includes adjusting image gamma of the digital image.

13. A system for enhancing digital images of a patient's eye during an eye surgery, the system comprising:

a modulable lighting source operable for illuminating the patient's eye with light;

a digital camera operable for collecting a digital image of the patient's eye as the patient's eye is illuminated by the light and tracked via motion tracking logic; and an electronic control unit (ECU) in communication with the digital camera and the modulable lighting source, wherein the ECU is configured to:

receive input signals, including a request to enhance an area-of-focus of the digital image;

identify the area-of-focus in response to the input signals;

in response to the input signals, selectively adjust respective characteristics of the modulable lighting source and digitally adjust characteristics of only those constituent pixels of the digital image that are located outside of the area-of-focus; and transmit display control signals to one or more display screens to thereby present an enhanced digital image of the patient's eye.

14. The system of claim 13, further comprising:

an ophthalmic microscope, wherein the modulable lighting source is connected to or integral with the ophthalmic microscope.

15. The system of claim 13, further comprising:

a microphone connected to the ECU, wherein the ECU is further configured to receive voice commands via the microphone from a surgeon performing the eye surgery, the input signals corresponding to the voice commands, and wherein the voice commands include an utterance or statement of a desired region of the patient's eye, the desired region including a pupil, an iris, a sclera, or a limbus region.

16. The system of claim 13, wherein the ECU is further configured to:

identify a stage of the eye surgery as an identified stage; and autonomously generate at least some of the input signals during the eye surgery based on the identified stage.

17. The system of claim 13, wherein the ECU is configured to selectively adjust the respective characteristics of the modulable lighting source and digitally adjust characteristics of only the constituent pixels of the digital image located outside of the area-of-focus by:

increasing a red light component of the modulable lighting source; and digitally reducing a brightness and/or color temperature of the constituent pixels of the digital image located outside of the area-of-focus.

18. The system of claim 13, wherein the ECU is further configured to:

detect a pigmentation color of an iris of the patient's eye; and selectively adjust one or more characteristics of the modulable lighting source by adjusting spectral characteristics of the modulable lighting source based on the pigmentation color.

19. A non-transitory computer-readable storage medium on which is recorded instructions for enhancing a digital image of a patient's eye during an ophthalmic procedure, wherein execution of the instructions by a processor causes the processor to:

receive the digital image of the patient's eye from a digital camera in communication with the processor as the patient's eye is illuminated by light from a modulable lighting source;

receive input signals from a surgeon performing the ophthalmic procedure, the input signals including a request to enhance an area-of-focus of the digital image, wherein the area-of-focus includes a pupil, an iris, a sclera, or a limbus region of the patient's eye;

identify the area-of-focus in response to the input signals;

selectively adjust respective characteristics of the modulable lighting source and digitally adjust characteristics of only those constituent pixels of the digital image that are located outside of the area-of-focus in response to the input signals; and transmit display control signals to one or more display screens to thereby present an enhanced digital image of the patient's eye.

20. The computer-readable storage medium of claim 19, wherein the processor is configured to adjust the respective characteristics of the modulable lighting source and digitally adjust characteristics of only those constituent pixels of the digital image that are located outside of the area-of-focus by:

increasing a red light component of the modulable lighting source as an increased red light component;

digitally reducing a brightness and/or color temperature of the constituent pixels of the digital image located outside of the area-of-focus while maintaining the increased red light component;

detecting a pigmentation color of the iris of the patient's eye; and selectively adjusting one or more characteristics of the modulable lighting source by adjusting spectral characteristics of the modulable lighting source based on the pigmentation color.

* * * * *